(12) United States Patent
Nielsen et al.

(10) Patent No.: US 10,695,504 B2
(45) Date of Patent: Jun. 30, 2020

(54) LOGGING DEVICE ADAPTED TO COMBINE DOSES

(71) Applicant: Novo Nordisk A/S, Bagsvaerd (DK)

(72) Inventors: Preben Mikael Nielsen, Holbaek (DK); Nikolaj Frogner Krusell, Risskov (DK); Jens Christian Andersen, Roskilde (DK); Nikolaj Eusebius Jakobsen, Soeborg (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 14/781,854

(22) PCT Filed: Apr. 3, 2014

(86) PCT No.: PCT/EP2014/056727
§ 371 (c)(1),
(2) Date: Oct. 1, 2015

(87) PCT Pub. No.: WO2014/161955
PCT Pub. Date: Oct. 9, 2014

(65) Prior Publication Data
US 2016/0030679 A1    Feb. 4, 2016

Related U.S. Application Data

(60) Provisional application No. 61/810,285, filed on Apr. 10, 2013.

(30) Foreign Application Priority Data

Apr. 5, 2013   (EP) ..................................... 13162513

(51) Int. Cl.
*A61M 5/315*    (2006.01)
*A61M 5/31*    (2006.01)
(Continued)

(52) U.S. Cl.
CPC .......... *A61M 5/31568* (2013.01); *A61M 5/20* (2013.01); *G06F 19/3456* (2013.01);
(Continued)

(58) Field of Classification Search
CPC .......... A61M 5/31568; A61M 2205/52; A61M 2005/3125; A61M 2005/3126
See application file for complete search history.

(56) References Cited

U.S. PATENT DOCUMENTS 5,509,905 A    4/1996   Michel
6,585,698 B1 *  7/2003  Packman ................ A61M 5/24
                                                            604/207

(Continued)

FOREIGN PATENT DOCUMENTS

CN      1820181 A    8/2006
CN    101912641 A   12/2010
(Continued)

OTHER PUBLICATIONS

Merriam-Webster.com, Definition of "estimate", https://www.merriam-webster.com/dictionary/estimate.*

*Primary Examiner* — Rebecca E Eisenberg
*Assistant Examiner* — Tasnim Mehjabin Ahmed
(74) *Attorney, Agent, or Firm* — Wesley Nicolas

(57) ABSTRACT

A drug delivery system comprises means to create a log of expelled dose amounts of drug. Stored dose amounts determined within a given time period are combined to a single combined dose amount. The given time period is initiated by a detected expelling event taking place (i) a given amount of time after a previous detected expelling event, or (ii) after a given detected action. By this arrangement it is possible to create a log corresponding to what a user considers to be a single dose, i.e. combining "split doses" to create a single log entry for a per se split dose.

14 Claims, 6 Drawing Sheets

(51) Int. Cl.
    *G06F 19/00* (2018.01)
    *A61M 5/20* (2006.01)
    *A61M 5/24* (2006.01)
(52) U.S. Cl.
    CPC ........... *G06F 19/3468* (2013.01); *A61M 5/24* (2013.01); *A61M 2005/2407* (2013.01); *A61M 2005/3125* (2013.01); *A61M 2005/3126* (2013.01); *A61M 2205/3592* (2013.01); *A61M 2205/50* (2013.01); *A61M 2205/52* (2013.01); *A61M 2205/60* (2013.01); *A61M 2205/6045* (2013.01); *A61M 2205/6072* (2013.01); *A61M 2205/6081* (2013.01)

(56) References Cited

U.S. PATENT DOCUMENTS

| | | | |
|---|---|---|---|
| 6,869,413 | B2 | 3/2005 | Langley et al. |
| 7,713,229 | B2 | 5/2010 | Veit et al. |
| 8,556,865 | B2 | 10/2013 | Peter et al. |
| 2004/0062148 | A1* | 4/2004 | Skyggebjerg ......... A61M 5/178 368/107 |
| 2005/0251103 | A1 | 11/2005 | Steffen et al. |
| 2009/0048565 | A1 | 2/2009 | Hansen |
| 2009/0318865 | A1 | 12/2009 | Moller et al. |
| 2010/0145656 | A1* | 6/2010 | Koehler ............. G06F 19/3468 702/182 |
| 2011/0015576 | A1 | 1/2011 | Plumptre et al. |
| 2011/0313350 | A1* | 12/2011 | Krulevitch .......... A61M 5/3129 604/65 |
| 2011/0313395 | A1* | 12/2011 | Krulevitch ............. A61M 5/24 604/504 |
| 2012/0072236 | A1* | 3/2012 | Atkin ................. A61M 5/3155 705/3 |
| 2013/0123685 | A1 | 5/2013 | Jespersen et al. |

FOREIGN PATENT DOCUMENTS

| | | |
|---|---|---|
| CN | 102458514 A | 5/2012 |
| CN | 102458533 A | 5/2012 |
| EP | 2060284 A1 | 5/2009 |
| JP | 2004516107 A | 6/2004 |
| JP | 2012519028 A | 8/2012 |
| JP | 2012183191 A | 9/2012 |
| WO | 02064196 | 8/2002 |
| WO | 2007107564 A1 | 9/2007 |
| WO | 2010052275 A2 | 5/2010 |
| WO | 2011/117212 A1 | 9/2011 |
| WO | 2011124711 A1 | 10/2011 |
| WO | 2012/001493 A2 | 1/2012 |
| WO | 2013004844 A1 | 1/2013 |
| WO | 2013050535 A2 | 4/2013 |

\* cited by examiner ns have been proposed which would help a user to generate, collect and distribute data indicative of the use of a given medical device.

For example, WO 2007/107564 describes an electronic "add-on" module adapted to be attached to and measure signals generated by a standard mechanical pen device, the module relying on e.g. the sounds inherently produced by such a device during operation.

Alternatively, in order to provide pre-filled drug delivery devices which more reliably allow detection of an out-dosed amount of drug, it has been proposed to modify such pre-filled drug delivery devices to provide them with structures making them more suitable for cooperation with external detection means, thereby providing more reliable and accurate determination of out-dosed drug amounts. For example, PCT/EP2012/069729 discloses a drug delivery device in which a rotating piston rod is provided with a magnet allowing an add-on logging module to detect the axial position of the magnet by means of 3D magnetometers.

Having regard to the above, it is an object of the present invention to provide systems, devices and methods allowing capturing and organizing drug delivery dose data in an efficient and user-friendly way.

LOGGING DEVICE ADAPTED TO COMBINE DOSES

CROSS-REFERENCE TO RELATED APPLICATIONS

This application is a 35 U.S.C. § 371 National Stage application of International Application PCT/EP2014/056727 (published as WO 2014/161955), filed Apr. 3, 2014, which claims priority to European Patent Application 13162513.9, filed Apr. 5, 2013; this application claims priority under 35 U.S.C. § 119 to U.S. Provisional Application 61/810,285; filed Apr. 10, 2013.

The present invention generally relates to medical devices for which the generation, collecting and storing of data are relevant. In specific embodiments the invention relates to devices and systems for capturing and organizing drug delivery dose data in an efficient and user-friendly way.

BACKGROUND OF THE INVENTION

In the disclosure of the present invention reference is mostly made to drug delivery devices comprising a threaded piston rod driven by a rotating drive member, such devices being used e.g. in the treatment of diabetes by delivery of insulin, however, this is only an exemplary use of the present invention.

Drug Injection devices have greatly improved the lives of patients who must self-administer drugs and biological agents. Drug Injection devices may take many forms, including simple disposable devices that are little more than an ampoule with an injection means or they may be durable devices adapted to be used with pre-filled cartridges. Regardless of their form and type, they have proven to be great aids in assisting patients to self-administer injectable drugs and biological agents. They also greatly assist care givers in administering injectable medicines to those incapable of performing self-injections.

Performing the necessary insulin injection at the right time and in the right size is essential for managing diabetes, i.e. compliance with the specified insulin regimen is important. In order to make it possible for medical personnel to determine the effectiveness of a prescribed dosage pattern, diabetes patients are encouraged to keep a log of the size and time of each injection. However, such logs are normally kept in handwritten notebooks, from the logged information may not be easily uploaded to a computer for data processing. Furthermore, as only events, which are noted by the patient, are logged, the note book system requires that the patient remembers to log each injection, if the logged information is to have any value in the treatment of the patient's disease. A missing or erroneous record in the log results in a misleading picture of the injection history and thus a misleading basis for the medical personnel's decision making with respect to future medication. Accordingly, it may be desirable to automate the logging of ejection information from medication delivery systems.

Though some injection devices integrate this monitoring/acquisition mechanism into the device itself, e.g. as disclosed in US 2009/0318865 and WO 2010/052275, most devices of today are without it. The most widely used devices are purely mechanical devices either durable or prefilled. The latter devices are to be discarded after being emptied and so inexpensive that it is not cost-effective to build-in electronic data acquisition functionality in the device it-self. Addressing this problem a number of solu-

DISCLOSURE OF THE INVENTION

In the disclosure of the present invention, embodiments and aspects will be described which will address one or more of the above objects or which will address objects apparent from the below disclosure as well as from the description of exemplary embodiments.

Thus, in a first aspect of the invention a logging device adapted to be releasably attached to a drug delivery device is provided, the drug delivery device comprising a drug reservoir or means for receiving a drug reservoir, and drug expelling means comprising dose setting means allowing a user to set a dose amount of drug to be expelled, the logging device comprising electronic circuitry adapted to create a log of expelled dose amounts of drug. The electronic circuitry comprises sensor means adapted to capture a property value related to the dose amount of drug expelled from a reservoir by the expelling means during an expelling event, processor means adapted to determine dose amounts based on captured property values, and storage means adapted to store a plurality of dose amounts to create the log. Stored dose amounts determined within a given time period are combined or can be combined to a single combined dose amount, wherein the given time period is initiated by a detected expelling event taking place a given amount of time after a previous detected expelling event, or after a given detected action.

When it is defined that a plurality of dose amounts are stored this covers that the dose amounts may be stored e.g. as native captured property values or as calculated dose amounts. The term "expelling event" refers to the expelling of drug taking place between a first state in which the expelling means is operated (e.g. by releasing a drive spring, by operating an electric motor, or by pushing a drive button) to begin expel drug and the first subsequent state in which operation is halted or stopped. Due to elastic properties of the system drug may continue to be expelled for a short period after a given event has ended.

When taking a dose of a given size the dose may be divided, e.g. by the user if the dose is large, or if the cartridge has to be changed. When an electronic logging device is provided this would result in a log with two entries although the user will consider the dose a single dose. By the above arrangement it is possible to create a log corresponding to what a user considers to be a single dose, i.e. combining "split doses" to create a single log entry for a per se split dose. As appears, each individual "split dose" represents an expelling event.

When two or more dose amounts are determined within a given time period they may be combined automatically, or the user may be prompted to accept that the two or more dose amounts determined within a given time period are combined. A determined dose amount below a given value, e.g. below 2 or 3 units of insulin, may be estimated to be a priming or an air shot and thus not stored or not combined as a log entry. When a combined dose amount is calculated and stored the individual doses may remain stored and subsequently retrieved when desired. A time value may be associated with each stored dose amount. For a combined dose e.g. the first time value may be used.

The logging device may be provided with a display controlled by the electronic circuitry and adapted to display stored data. For example, a log entry may be shown as a drug amount together with a time value. The time may be a real time value or the time since a given dose amount was stored. Combined amounts may be indicated as such. Further or alternatively, the electronic circuitry may comprise transmitter means adapted to transmit stored data to an external receiver, e.g. by means of near field communication (NFC).

In an exemplary embodiment the sensor means is adapted to capture a property value in the form of an amount of rotation of a magnetic member arranged in the drug delivery device, the amount of rotation of the magnetic member corresponding to the amount of drug expelled from a reservoir by the expelling means.

The above-described logging device may be provided in combination with a drug delivery device, thereby forming a drug delivery system, the drug delivery device comprising a drug reservoir or means for receiving a drug reservoir, as well as drug expelling means, wherein the logging device is releasably attachable to the drug delivery device.

The system may further comprise a cap releasably attachable to the drug delivery device to cover an outlet portion of a drug reservoir, the logging device being adapted to detect when the cap is attached, whereby attachment of the cap provides that a running time period is ended and the dose amounts detected since the time period was initiated are combined.

In an exemplary embodiment the drug delivery device further comprises an identifier, e.g. a colour or in the form of a barcode, representing information for the specific drug type contained in the reservoir or the specific drug delivery device, with the logging device further comprising means for capturing information from the identifier, wherein the electronic circuitry is adapted to create a log for a given identifier.

In a further aspect of the invention a drug delivery system is provided, comprising a drug reservoir or means for receiving a drug reservoir, drug expelling means comprising dose setting means allowing a user to set a dose amount of drug to be expelled, and electronic circuitry adapted to create a log of expelled dose amounts of drug. The electronic circuitry comprises sensor means adapted to capture a property value related to the dose amount of drug expelled from a reservoir by the expelling means during an expelling event, processor means adapted to determine dose amounts based on captured property values, and storage means adapted to store a plurality of dose amounts to create the log. In such a system dose amounts determined within a given time period are combined or can be combined to a single combined dose amount, wherein the given time period is initiated by a detected expelling event taking place a given amount of time after a previous detected expelling event, or after a given detected action.

The system may be in the form of an integrated drug delivery device comprising the drug reservoir or means for receiving a drug reservoir, the drug expelling means, and the electronic circuitry. The integrated device may be provided with the above-described features of a separate logging device.

In order to capture a property value related to a dose amount of drug expelled a number of technologies could be used. For example, for an integrated arrangement capture could be based on galvanic contacts, optical sensors or magnetic sensors. Indeed, for an external attachable logging device the same principles could be used, however, by using magnetic detection it would be possible to detect movements inside the delivery device without having to provide openings or contacts in the housing wall. For a given expelling mechanism a number of components will normally be moved corresponding to an expelled amount of drug, e.g. a piston rod will move axially and a drive member for moving the piston rod may rotate. Correspondingly, a property value could be either axial displacement or amount of rotation, or a combination of both. For example, if a given component may rotate more than 360 degrees in order to expel a given dose, the amount of rotation may be captured by counting increments or, alternatively, by determining the rotational position of the rotating component and combine it with information relating to the number of full rotations or the axial position of an axially moved component.

In the context of the present application and as used in the specification and the claims, the term processor means covers any combination of electronic circuitry suitable for providing the specified functionality, e.g. processing and storing data as well as controlling all connected input and output devices. A processor will typically comprise one or more CPUs or microprocessors which may be supplemented by additional devices for support, storage or control functions. For example, in case a communication interface is provided (e.g. wireless), the transmitter and receiver may be fully or partly integrated with a processor, or may be provided by individual units. Each of the components making up the processor circuitry may be special purpose or general purpose devices. The term display means covers any type of display capable of visually providing the specified functionality, e.g. a LCD or OLED.

As used herein, the term "insulin" is meant to encompass any drug-containing flowable medicine capable of being passed through a delivery means such as a cannula or hollow needle in a controlled manner, such as a liquid, solution, gel or fine suspension, and which has a blood glucose controlling effect, e.g. human insulin and analogues thereof as well as non-insulins such as GLP-1 and analogues thereof. In the description of exemplary embodiments reference will be made to the use of insulin.

BRIEF DESCRIPTION OF THE DRAWINGS

In the following the invention will be further described with reference to the drawings, wherein.

In the figures like structures are mainly identified by like reference numerals.

DESCRIPTION OF EXEMPLARY EMBODIMENTS

When in the following terms such as "upper" and "lower", "right" and "left", "horizontal" and "vertical" or similar relative expressions are used, these only refer to the appended figures and not necessarily to an actual situation of use. The shown figures are schematic representations for which reason the configuration of the different structures as well as their relative dimensions are intended to serve illustrative purposes only.

Figure 1A:
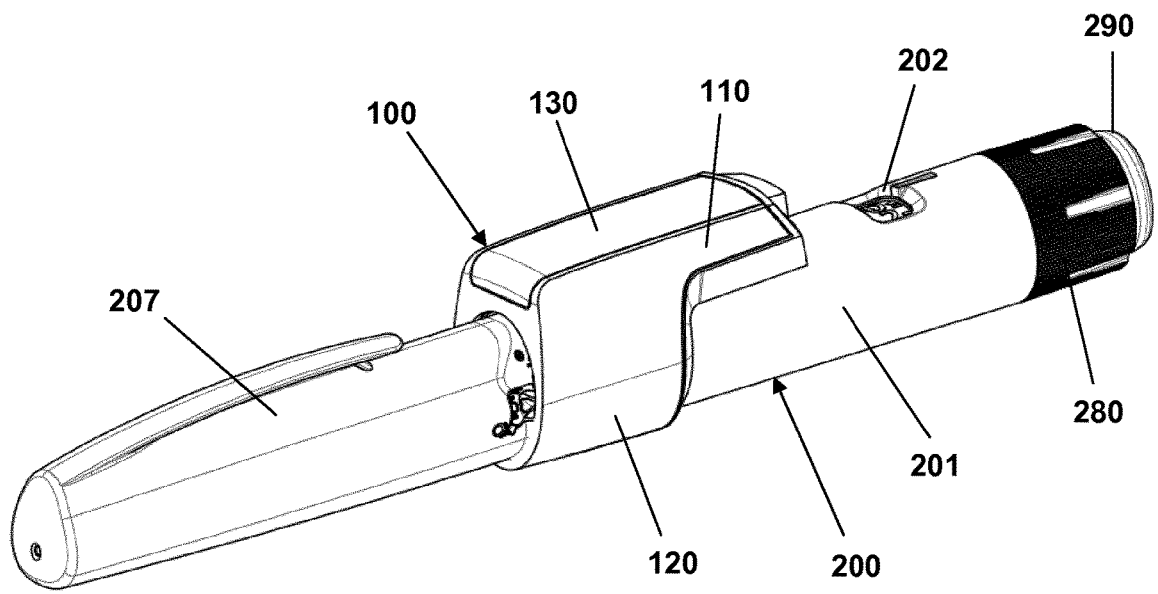
FIGS. 1A and 1B show a pen-formed drug delivery device with an electronic logging module.
Figure 1B:
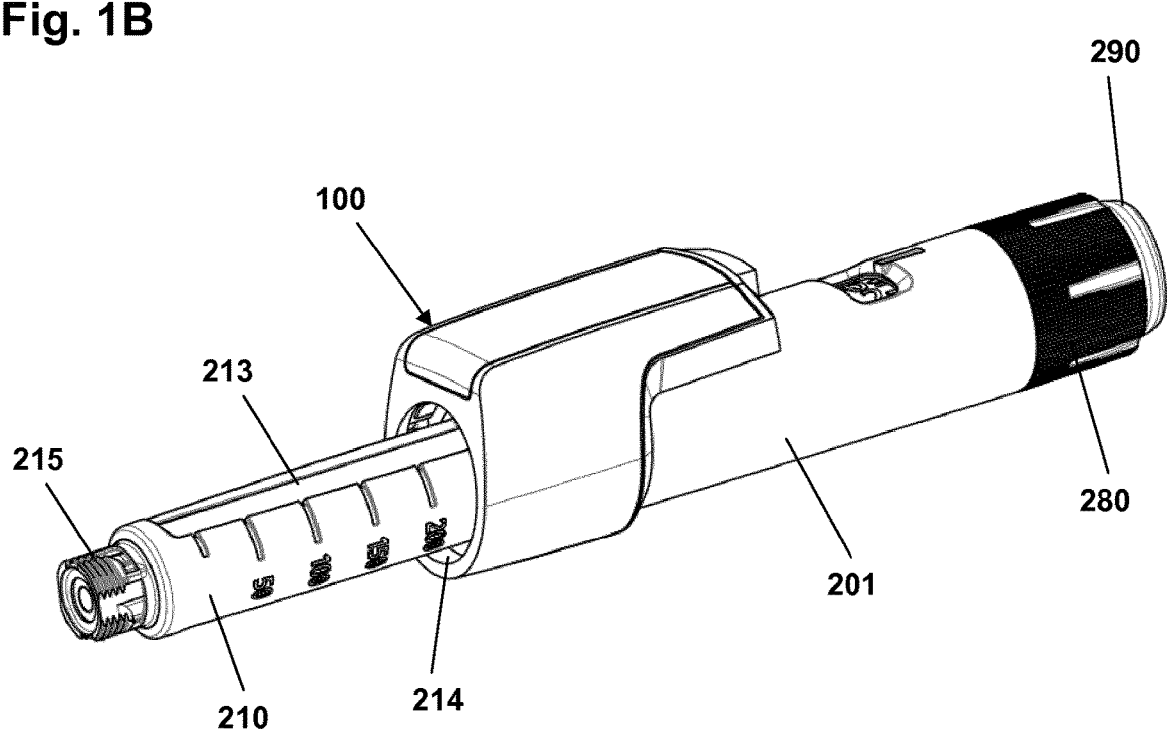

FIGS. 1A and 1B show a pen-formed drug delivery device 200 on which an electronic logging module 100 is mounted. In the present context the device represents a "generic" drug delivery device providing a specific example of a device in combination with which embodiments of the present invention is intended to be used or which can form a basis for aspects of the present invention.

More specifically, the logging module 100 comprises a body portion 110 and a ring-formed portion 120 allowing the module to be mounted on a generally cylindrical pen device. The body portion comprises electronic circuitry and sensor means allowing a property to be detected representing an amount of drug being expelled from the cartridge, as well as a display 130 for displaying data to a user. The ring portion comprises coupling means allowing the module to be securely and correctly mounted on the pen body. The electronic circuitry and the sensor means may in part be arranged in the ring portion.

The pen device 200 comprises a cap part 207 and a main part having a proximal body or drive assembly portion with a housing 201 in which a drug expelling mechanism is arranged or integrated, and a distal cartridge holder portion in which a drug-filled transparent cartridge 213 with a distal needle-penetrable septum is arranged and retained in place by a non-removable cartridge holder attached to the proximal portion, the cartridge holder having openings allowing a portion of the cartridge to be inspected as well as distal coupling means 215 allowing a needle assembly to be releasably mounted. The cartridge is provided with a piston driven by a piston rod forming part of the expelling mechanism and may for example contain an insulin, GLP-1 or growth hormone formulation. A proximal-most rotatable dose member 280 serves to manually set (or dial) a desired dose of drug shown in display window 202 and which can then be expelled when the button 290 is actuated. Depending on the type of expelling mechanism embodied in the drug delivery device, the expelling mechanism may comprise a spring as in the shown embodiment which is strained during dose setting and then released to drive the piston rod when the release button is actuated. Alternatively the expelling mechanism may be fully manual in which case the dose member and the actuation button moves proximally during dose setting corresponding to the set dose size, and then is moved distally by the user to expel the set dose.

FIGS. 1A and 1B show a drug delivery device of the pre-filled type, i.e. it is supplied with a pre-mounted cartridge and is to be discarded when the cartridge has been emptied. In alternative embodiments the drug delivery device may be designed to allow a loaded cartridge to be replaced, e.g. in the form of a "rear-loaded" drug delivery device in which the cartridge holder is adapted to be removed from the device main portion, or alternatively in the form of a "front-loaded" device in which a cartridge is inserted through a distal opening in the cartridge holder which is non-removable attached to the main part of the device.

Figure 2:
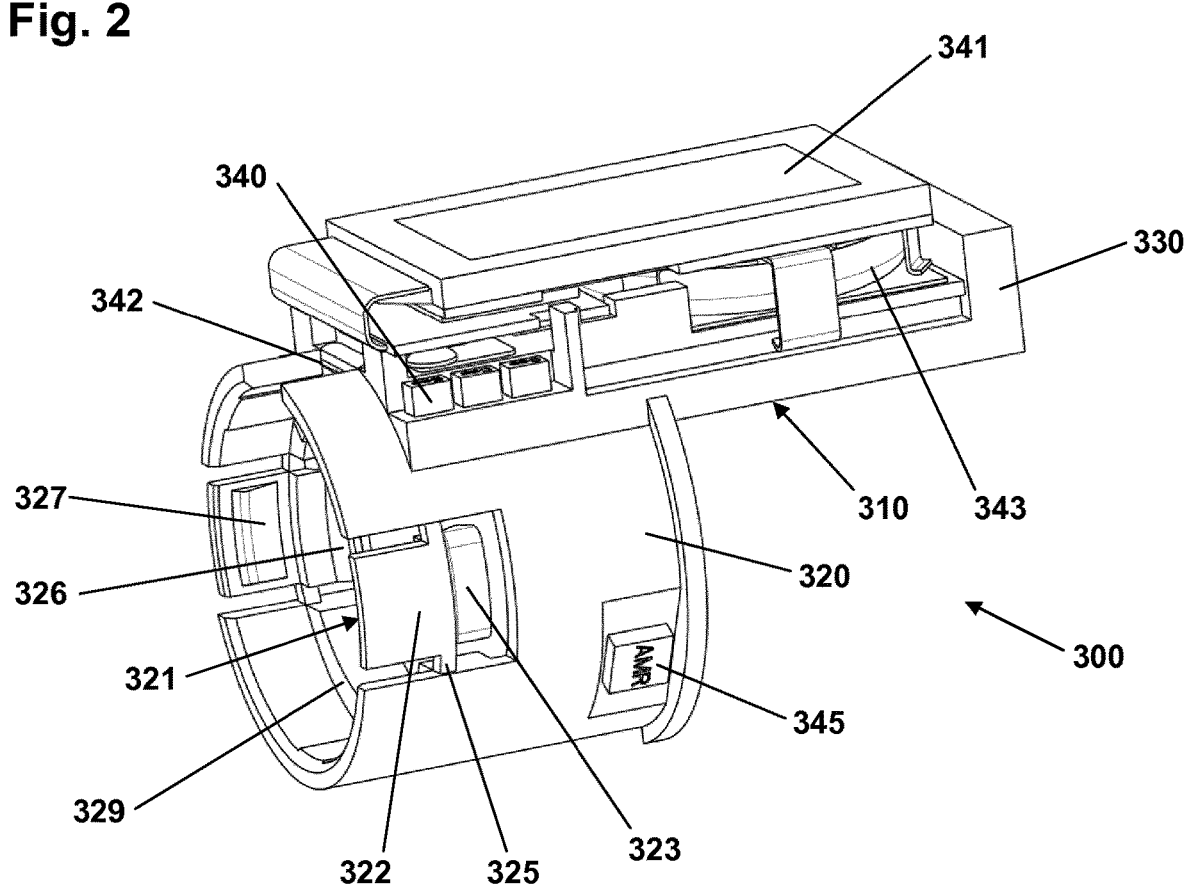
FIG. 2 shows the interior of a logging module.

Turning to FIG. 2 an exemplary embodiment of a logging module 300 is shown in which the exterior housing has been removed to reveal the interior design and components. The module comprises a main body 310 having a generally cylindrical ring-formed portion 320 and a body portion 330 on which the majority of the electronic circuitry is mounted. The main body is formed from a LDS polymer whereby integrated wiring can be achieved by using LDS (Laser Direct Structuring) technology, the polymer having elastic properties allowing a flexible hinged latch to be formed integrally. More specifically, the ring portion comprises an inner generally cylindrical surface adapted to be mounted on a drug delivery pen body as well as a pair of opposed integrally formed coupling structures 321 adapted to engage corresponding coupling structures on the pen device to assure that the module is securely mounted. The distal part of the ring portion has a larger diameter with a distally facing circumferential stop surface 329 adapted to receive and engage a cap when the module is mounted on a pen as can be seen in FIG. 1B.

The inner ring surface and the outer pen body surface may be in either form-fitting or slight frictional engagement. Each coupling structure on the module is in the form of a latch 322 having a proximal portion 323, a distal portion 324 and a central portion, the latter being pivotally connected to the ring portion by integrally formed flexible hinges 325 allowing the latch to pivot a few degrees corresponding to a circumferential axis. By this arrangement the distal latch portion moves inwards when the proximal portion is moved outwards and vice versa. The proximal latch portions each comprises an inner protrusion 326 adapted to engage a corresponding coupling structure on the pen device and the distal latch portions each comprises a protrusion 327 adapted to engage the cap when a cap is mounted on the pen body by insertion into the circumferential gap 214 (see FIG. 1B) between the logging module and the cartridge holder. To assure correct rotational mounting of the module on the pen the module is provided with a slot (not to be seen) adapted to axially engage a corresponding protrusion on the pen. In the shown embodiment of FIG. 1A the protrusion is provided on the pen cartridge holder 210 and arranged opposite the pen display window 202, the electronic display 130 thereby being arranged next to the pen display window when the module is mounted on a pen. On the body portion 330 the majority of the electronic components 340, a display 341, a cap switch 342 and a battery 343 are mounted. In the shown embodiment the logging module comprises three circumferentially arranged sensors in the form of magnetometers 345 mounted directly on the ring portion 320, the sensors as well as the majority of the electronic components being connected using LDS. The magnetometers and the electronic circuitry are adapted to detect and capture a property value related to the dose amount of drug expelled in the form of rotational movement of a magnetic member of the enclosed expelling mechanism, for example as described in greater detail in EP patent application 13162517.0. Further sensors may be provided allowing e.g. the type of the device to be recognized. For example, a sensor may be provided adapted to detect the colour of the part of the pen on which the logging module is attached or to read a correspondingly arranged barcode.

The logging module may be provided with user input means in the form of e.g. one or more buttons (not shown) allowing the user to control the module, e.g. allowing the user to toggle through log entries. The logging module may further be provided with transmission means allowing data to be transmitted to or from the module, e.g. log data may be transmitted to a user's smartphone by NFC or other wireless means.

Figure 3:
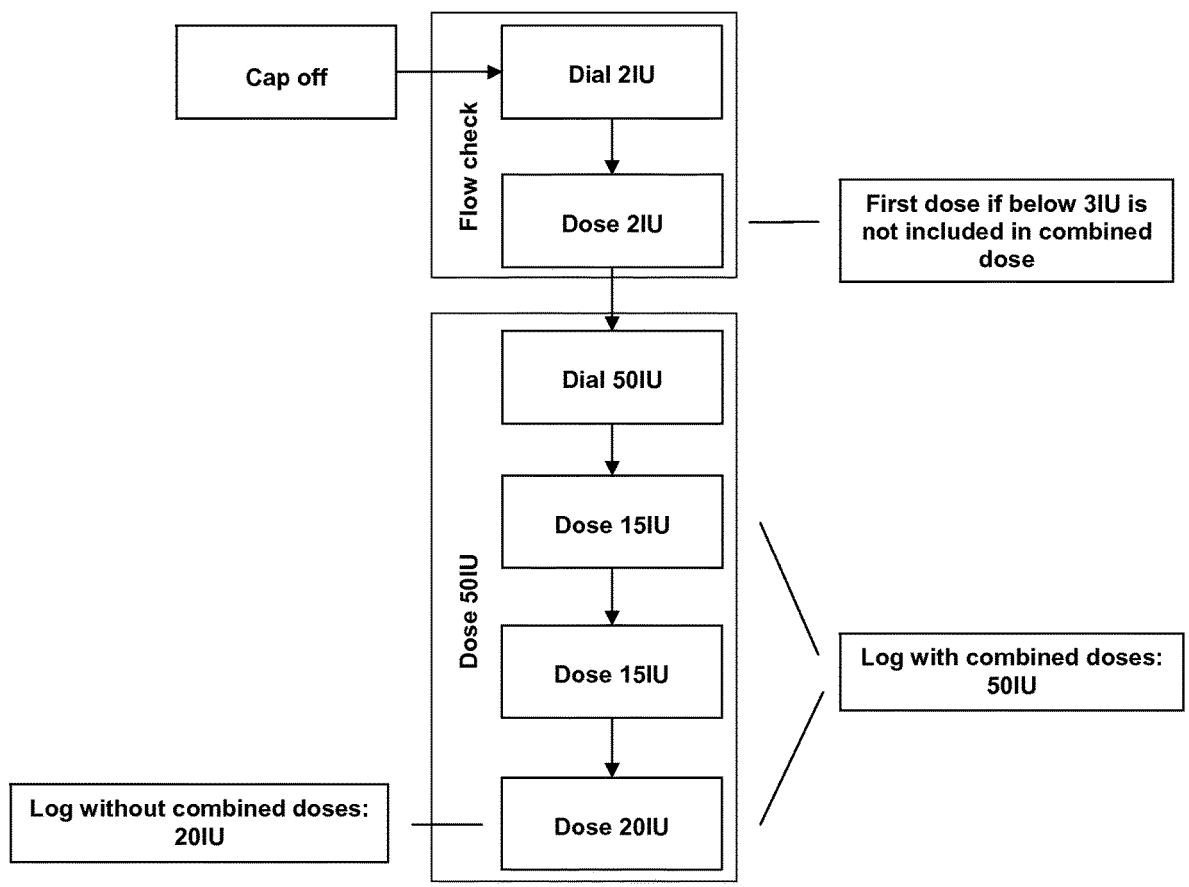
FIG. 3 shows a flowchart for an exemplary use of a drug delivery device with logging means.

With reference to FIGS. 1-3 an example of use of the above-described assembly to expel an amount of an insulin formulation will be described. First the user removes the cap from the assembly whereby the logging module is turned on by means of the cap switch 342. The display may show different messages, e.g. the last log entry. For the described embodiment the display is muted after e.g. 5 seconds and will stay muted until the cap is put back in place, this indicating that the user has taken the desired dose. This procedure can also be used if the user wants to check the log entry for the last dose. If not in place a needle assembly is mounted on the cartridge holder coupling 215 after which a flow check can be performed by setting and expelling a small dose of e.g. 2 units (IU) of insulin. The expelled dose is detected by the logging module, however, in the shown embodiment the logging module is adapted to recognise small doses of e.g. 3 IU or less as related to flow check operations for which reason they are not stored as a log entry. After the flow check has been performed the user sets a desired dose of here 50 IU. As this is a relatively large dose the user decides to split the dose and expel (and inject) it as three smaller doses of respectively 15 IU, 15 IU and 20 IU as shown over e.g. 1 minute. When the first dose was expelled the time window for combining doses, e.g. 5 minutes, was initiated this providing that the 3 doses are combined to a single dose of 50 IU in the log. The time associated with the combined log could be e.g. the time for the last dose. When the user puts the cap back in place the log entry of the combined dose of 50 IU is displayed. If the doses had not been combined the last log entry would have been 20 IU which may mislead the user to think that not the entire dose of 50 IU was taken, this increasing the risk of unintended overdosing.

Figure 4:
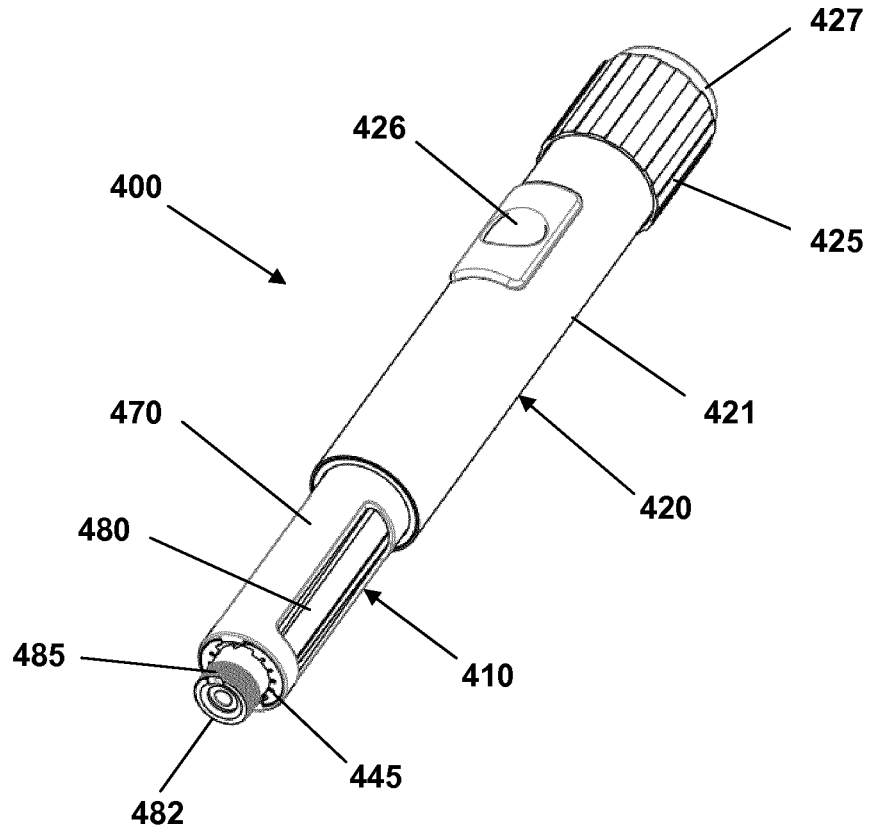
FIGS. 4 and 5 show a pen-formed drug delivery device with an integrated logging module.
Figure 5:
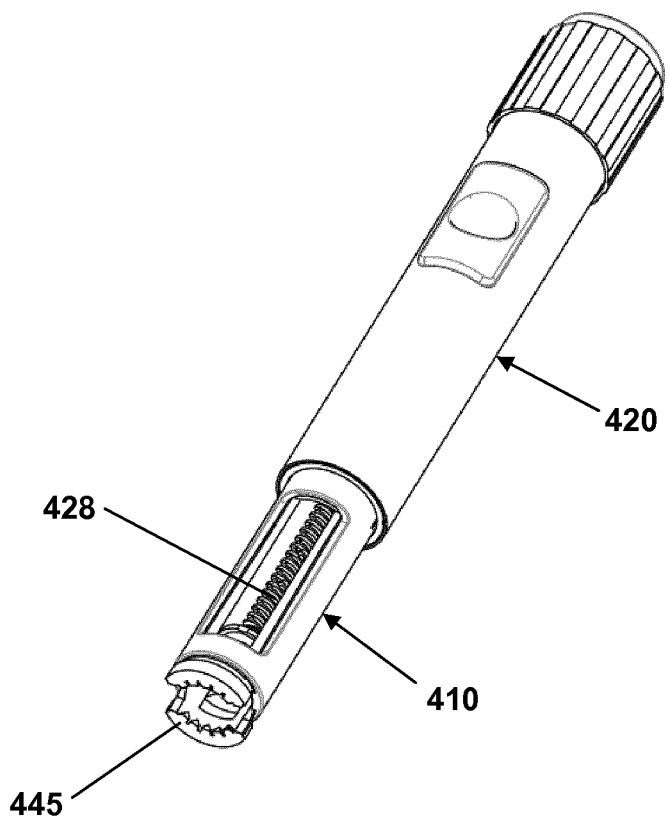

With reference to FIGS. 4 and 5 an embodiment of a drug delivery system in which the logging module is integrated in the pen-formed drug delivery device will be described.

More specifically, the pen device comprises a cap part (not shown) and a main part having a proximal body or drive assembly portion 420 with a housing 421 in which a drug expelling mechanism is arranged or integrated, and a distal cartridge holder portion in which a drug-filled transparent cartridge 480 with a distal needle-penetrable septum can be arranged and retained in place by a cartridge holder 410 attached to the proximal portion, the cartridge holder having openings allowing a portion of the cartridge to be inspected. The device is designed to be loaded by the user with a new cartridge through a distal receiving opening in the cartridge holder, the cartridge being provided with a piston driven by a piston rod 428 forming part of the expelling mechanism. A proximal-most rotatable dose ring member 425 serves to manually set a desired dose of drug shown in display window 426 and which can then be expelled when the release button 427 is actuated. Depending on the type of expelling mechanism embodied in the drug delivery device, the expelling mechanism may comprise a spring which is strained during dose setting and then released to drive the piston rod when the release button is actuated. Alternatively the expelling mechanism may be fully manual in which case the dose ring member and the release button moves proximally during dose setting corresponding to the set dose size, and then moved distally by the user to expel the set dose. The cartridge is provided with distal coupling means in the form of a needle hub mount 482 having, in the shown example, an external thread 485 adapted to engage an inner thread of a corresponding hub of a needle assembly. In alternative embodiments the thread may be combined with or replaced by other connection means, e.g. a bayonet coupling.

The cartridge holder comprises a distal opening adapted to receive a cartridge. More specifically, the cartridge holder comprises an outer rotatable tube member 470 operated by the user to control movement of gripping means to thereby open and close gripping shoulders 445 configured to grip and hold a cartridge. FIG. 5 shows the device with the cartridge removed and the gripping shoulders in their un-locked "open" position in which a cartridge can be removed and a new inserted.

As appears, FIG. 4 shows a drug delivery device of the front-loaded type in which a cartridge is inserted through a distal opening in the cartridge holder which in non-removable attached to the main part of the device, however, the drug delivery device may alternatively comprise a cartridge holder adapted to be removed from the device main portion and in which a cartridge is received and removed through the proximal opening.

Figure 6:
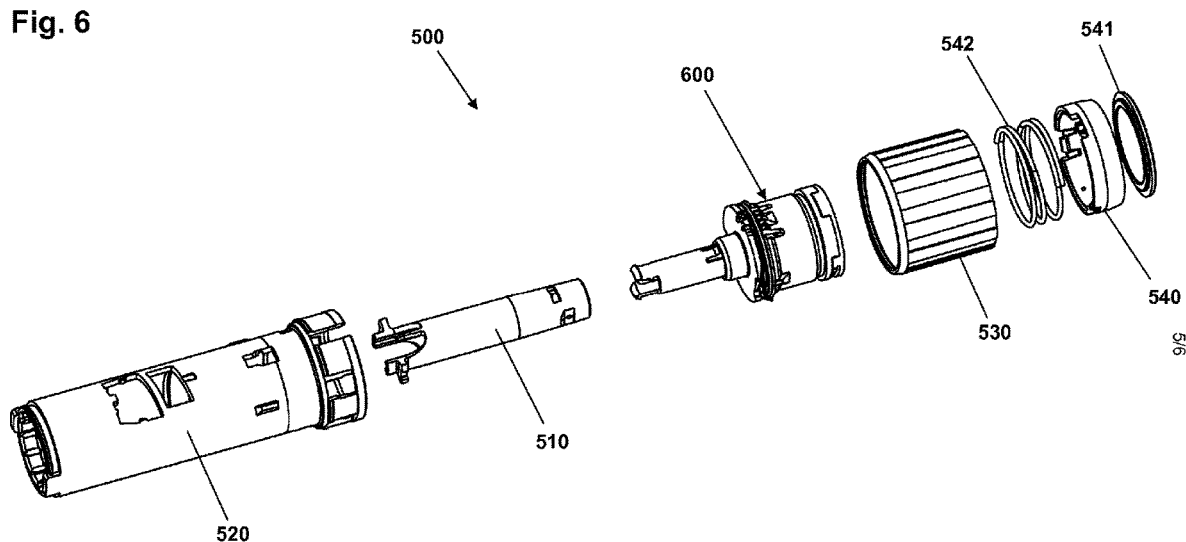
FIG. 6 shows a logging module adapted to be incorporated in a drug delivery device.

With reference to FIG. 6 a subassembly 500 for a drug delivery device will be described, the subassembly comprising a logging module in combination with parts of the drug delivery device being directly functionally related to the incorporation and operation of logging unit. More specifically, the subassembly comprises an electronically controlled logging module 600, an inner tube member 510, a generally cylindrical inner housing member 520, a dial ring member 530 and a button assembly comprising a button ring 540, a button window 541 and a button spring 542. The inner housing member is configured to be arranged inside an outer housing member providing the exterior of the drug delivery device.

Whereas the logging module of FIGS. 1 and 2 is based on contact-less detection of movements inside the pen device, then the logging module of FIGS. 4-6 mechanically engages the expelling mechanism in order to detect rotational movement of a component of the mechanism. In the shown embodiment a rotary sensor is provided for detection of rotation between a rotating member of the expelling mechanism and the logging module which, apart from a rotary sensor portion connected to the rotating expelling member, is arranged non-rotational in the housing. The shown logging module is described in greater detail in EP patent application 13162517.0.

In an exemplary embodiment the rotary sensor is designed to count the number of steps during setting and to count down the number of steps during expelling, with the expelling steps being registered in the log as the dose being expelled. By counting in both directions proper registering and functioning of the logging module can be assured to a high degree. As a given dose of drug, especially if large, may be divided and injected with a given pause, the logging module is programmed to log two dose amounts expelled within a given time window, e.g. 5 minutes, as one dose.

The logging module may be configured to store and show data in different ways. To many users the time since last dose and the size of that dose are the most important values. To other users and/or a medical practitioner an overview of the entire log for a given period, e.g. a week or a month, may be of importance. To allow such an overview the logging module may be provided with output means allowing the dose log to be transferred, e.g. by NFC transfer, to an external display device, e.g. a smartphone or computer for better graphic overview.

To ensure that the full dose is expelled the logging module may be set up to display the last expelled dose only when the expelling mechanism has been returned to zero. Otherwise a given "half" dose will be stored in the log but not displayed. For example, if a dose of 40 IU is dialled and 20 IU are expelled immediately thereafter the display will not show data for that delivery. To have the dose shown in the display the user may expel the remaining dose and the combined dose of 40 IU together with a time stamp will be shown in the display. Alternatively the user may dial the expelling mechanism back to zero and the display will show 20 IU, or the user may dial the expelling mechanism back to 10 IU and expel the 10 IU and the display will show 30 IU. Indeed, for the expelled amounts to be combined the two (or more) doses will have to be expelled within the above-described time window, e.g. 5 minutes. Otherwise only the last portion of the dose will be displayed, the first portion being stored merely as an entry in the log.

The display can be configured to show data in different formats. For example, the display may have two lines in which time is shown using a HH:MM:SS stop watch design, this providing that the time since the last dose expelled from the device can be shown with a running second counter allowing a user to easily identify the shown information as a counting time value. After 24 hours the display may continue to display time in the HH:MM:SS format or change to a day and hour format.

To save energy the display will turn off after a predetermined amount of time, e.g. 30 seconds. To turn on the display again the user may e.g. press the button or the display may be turned on when the dose dial is turned away from and then back to zero.

A user may desire to check the dose log directly on the module display. Toggling through the dose log could also be controlled by the axial switch, e.g. two fast pushes on the button 427 will bring the module into log display mode, each consecutive push on the button recalling the next log entry. The module may leave the log display mode automatically after a given amount of time, or the user may bring the module into normal display mode by e.g. dialing back and forth as described above. As an alternative, the electronic module may be provided with other types of input means, e.g. a motion sensor which would allow a user to turn on the display by shaking or tapping, or a touch sensor integrated in the display as is well known from e.g. smartphones which would allow a user to turn on the display by swiping a finger across the display.

Figure 7:
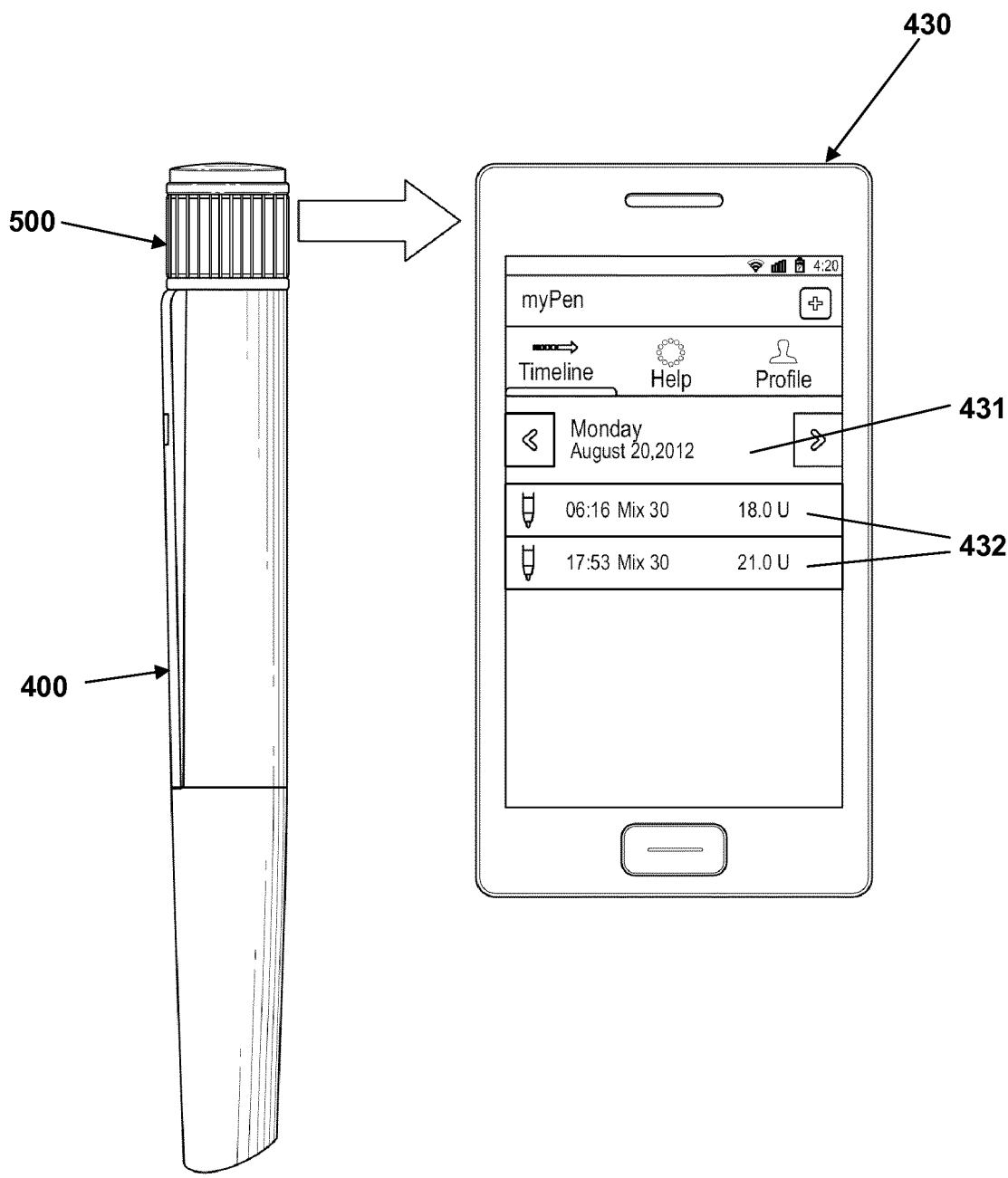
FIG. 7 shows a drug delivery pen provided with a logging module and in communication with a smartphone.

FIG. 7 shows a drug delivery pen 400 provided with a logging module 500 of the type described above with reference to FIGS. 4-6 and arranged next to a smartphone 430 configured to receive logging data from the logging module via wireless communication, e.g. NFC. As appears, the logging module is provided with a display configured to indicate the size of the last dose and the time since the last dose using the stopwatch display mode.

In order to communicate with the logging module the smartphone has been provided with specific "insulin diary" software. When the software is activated to initiate data transfer the smartphone NFC transmitter will transmit specific code which will wake up any nearby logging module which will then retransmit a unique code identifying the specific module. If a specific code is received for the first time the user is asked to confirm pairing and is asked to select from a list the given drug that should be associated with the given logging module, e.g. "Mix 30" as shown. In this way the smartphone can create an insulin diary covering more than one drug. In the described simple "manual" set-up the user has to ensure that a correct cartridge, e.g. with Mix 30 insulin, is loaded in a drug delivery pen which has been associated with that type of drug. Indeed, other set-ups can be envisaged, e.g. a given pen may be (mechanically) coded to only accept a given type of cartridge with the designated type of drug, or the pen and logging module may be provided with the ability to identify different types of cartridges and thus types of drug.

In the shown embodiment log data from a logging module associated with a Mix 30 insulin has been transferred. In the exemplary user interface the user can toggle back and forth between different day views, each day view showing the different amounts of drug delivered together with a real time value. In FIG. 7 on a given day 431 first and second amounts 432 of Mix 30 has been delivered with the time and amount shown for each delivery. It may be indicated if a given dose amount is based on combined dose amounts.

In the above description of exemplary embodiments, the different structures and means providing the described functionality for the different components have been described to a degree to which the concept of the present invention will be apparent to the skilled reader. The detailed construction and specification for the different components are considered the object of a normal design procedure performed by the skilled person along the lines set out in the present specification.

The invention claimed is:

1. A logging device adapted to be releasably attached to a drug delivery device, the drug delivery device comprising a drug reservoir or structure for receiving a drug reservoir, and a drug expelling structure comprising dose setting structure allowing a user to set a dose amount of drug to be expelled, the logging device comprising:
  electronic circuitry adapted to create a log of expelled dose amounts of drug,
  comprising:
    one or more sensors adapted to capture, when the logging device is attached to the drug delivery device, a property value related to the dose amount of drug expelled from the reservoir by the expelling structure during an expelling event,
    a processor adapted to determine dose amounts based on captured property values, and
    a storage device adapted to store a plurality of dose amounts to create the log,
  wherein the logging device is configured to:
  upon detecting the expelling event, said expelling event taking place a given amount of time after a previous detected expelling event, or after a given detected action, initiate tracking for a predefined time period; and
  upon conclusion of the predefined time period, update or prompt the user to update the log with a combined entry corresponding to the combination of the stored dose amounts logged within the predefined time period.

2. The logging device of claim 1, wherein the logging device is adapted so that two or more dose amounts determined within the predetermined time period are automatically combined.

3. The logging device of claim 1, wherein the logging device is adapted to prompt the user to accept that two or more dose amounts determined within the predetermined time period are combined.

4. The logging device of claim 1, wherein the logging device is adapted so that a determined dose amount below a given value is not stored or combined as a log entry.

5. The logging device of claim 1, wherein the log comprises a time value associated with each stored dose amount.

6. The logging device of claim 1, further comprising:
a display controlled by the electronic circuitry and adapted to display a stored dose amount.

7. The logging device of claim 1, wherein the one or more sensors are adapted to capture the property value in the form of an amount of rotation of a magnetic member arranged in the drug delivery device, the amount of rotation of the magnetic member corresponding to the amount of drug expelled from the reservoir by the expelling structure.

8. The logging device of claim 1, in combination with the drug delivery device, thereby forming a drug delivery system, the drug delivery device comprising:
the drug reservoir or structure for receiving a drug reservoir,
the drug expelling structure,
wherein the logging device is releasably attachable to the drug delivery device.

9. The drug delivery system of claim 8, further comprising a cap releasably attachable to the drug delivery device to cover an outlet portion of the drug reservoir, the logging device being adapted to detect when the cap is attached,
whereby attachment of the cap provides that a running time period is ended and the dose amounts detected since the predetermined time period was initiated are combined.

10. The drug delivery system of claim 8, the drug delivery device further comprising:
an identifier representing information for a specific drug type contained in the reservoir or the specific drug delivery device,
wherein at least one of the one or more sensors is adapted to capture information from the identifier.

11. The drug delivery system of claim 10, wherein the identifier is a colour or in the form of a barcode.

12. A drug delivery system, comprising:
a drug reservoir or structure for receiving a drug reservoir,
a drug expelling structure comprising dose setting structure allowing a user to set a dose amount of drug to be expelled,
electronic circuitry adapted to create a log of expelled dose amounts of drug, comprising:
one or more sensors adapted to capture a property value related to the dose amount of drug expelled from the reservoir by the expelling structure during an expelling event,
a processor adapted to determine dose amounts based on captured property values, and
a storage device adapted to store a plurality of dose amounts to create the log,
wherein the electronic circuitry is configured to:
upon detecting the expelling event, said expelling event taking place a given amount of time after a previous detected expelling event, or after a given detected action, initiate tracking for a predefined time period; and
upon conclusion of the predefined time period, update or prompt the user to update the log with a combined entry corresponding to the combination of the stored dose amounts logged within the predefined time period.

13. The drug delivery system of claim 12, wherein the one or more sensors are adapted to capture the property value in the form of an amount of rotation of a magnetic member arranged in the drug delivery device, the amount of rotation of the magnetic member corresponding to the amount of drug expelled from the reservoir by the expelling structure.

14. The drug delivery system of claim 12, wherein two or more dose amounts determined within the predetermined time period are combined automatically.

* * * * *

UNITED STATES PATENT AND TRADEMARK OFFICE
CERTIFICATE OF CORRECTION

| | |
|---|---|
| PATENT NO. | : 10,695,504 B2 |
| APPLICATION NO. | : 14/781854 |
| DATED | : June 30, 2020 |
| INVENTOR(S) | : Nielsen et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 337 days.

Signed and Sealed this
Twenty-third Day of November, 2021

Drew Hirshfeld
*Performing the Functions and Duties of the*
*Under Secretary of Commerce for Intellectual Property and*
*Director of the United States Patent and Trademark Office*